United States Patent
Kurihara (10) Patent No.: US 8,679,084 B2
(45) Date of Patent: Mar. 25, 2014

(54) ABSORBENT ARTICLE

(75) Inventor: Ryoko Kurihara, Sakura (JP)

(73) Assignee: Daio Paper Corporation, Ehime (JP)

( * ) Notice: Subject to any disclaimer, the term of this patent is extended or adjusted under 35 U.S.C. 154(b) by 376 days.

(21) Appl. No.: 12/995,406

(22) PCT Filed: May 27, 2009

(86) PCT No.: PCT/JP2009/059687
§ 371 (c)(1),
(2), (4) Date: Dec. 10, 2010

(87) PCT Pub. No.: WO2009/145222
PCT Pub. Date: Dec. 3, 2009

(65) Prior Publication Data
US 2011/0077613 A1    Mar. 31, 2011

(30) Foreign Application Priority Data

May 30, 2008    (JP) .................................. 2008-141911

(51) Int. Cl.
*A61F 13/15*    (2006.01)
*A61F 13/20*    (2006.01)
(52) U.S. Cl.
USPC .................................................... 604/385.24
(58) Field of Classification Search
USPC ............. 604/385.04, 385.26, 385.28, 385.24, 604/385.25, 385.27
See application file for complete search history.

(56) References Cited

U.S. PATENT DOCUMENTS

| | | | |
|---|---|---|---|
| 6,569,140 B1 | 5/2003 | Mizutani et al. | |
| 2004/0030317 A1* | 2/2004 | Torigoshi ................. | 604/385.27 |
| 2004/0249355 A1* | 12/2004 | Tanio et al. .............. | 604/385.01 |

FOREIGN PATENT DOCUMENTS

| | | |
|---|---|---|
| JP | 64-068503 | 3/1989 |
| JP | 2001-095842 | 4/2001 |
| JP | 2001-145667 | 5/2001 |
| JP | 2002-000656 | 1/2002 |
| JP | 2002-165836 | 6/2002 |
| JP | 2006-280580 | 10/2006 |
| JP | 2006-280583 | 10/2006 |
| JP | 2007-089819 | 4/2007 |
| JP | 2008-125918 | 6/2008 |

* cited by examiner

*Primary Examiner* — Jackie Ho
*Assistant Examiner* — Peter S Vasat
(74) *Attorney, Agent, or Firm* — Jordan and Hamburg LLP (57) ABSTRACT

In a three-dimensional gather BS, a sheet extending from the lateral side to the center side direction is folded in four by folding the sheet at the first folding portion folded back toward the lateral side on a central side position and at the second folding portion and the third folding portion in series to form the first folding back surface, the second folding back surface, the third folding back surface, and the fourth folding back surface. In a predetermined range containing the body fluid excretion portion, at least the third folding back surface and the fourth folding back surface stand so as to form an approximately dogleg-shaped cross section, and in the buttock side portion, the second folding back surface to the fourth folding back surface are bonded to one another, and stand linearly in an oblique manner toward the outer side direction.

4 Claims, 9 Drawing Sheets

(PRIOR ART)

ABSORBENT ARTICLE

BACKGROUND OF THE INVENTION

The present invention mainly relates to an absorbent article, such as a sanitary napkin, a pantiliner, a vaginal discharge sheet, an incontinence pad, or a toiletry, and, specifically, relates to structures of three-dimensional gathers formed on both side ends on the top surface side of the absorbent article.

As absorbent articles such as sanitary napkins, pantiliners, and incontinence pads, conventionally known are those each having a liquid-impermeable back sheet of a polyethylene sheet, a polyethylene laminated nonwoven fabric, or the like; a liquid-permeable top sheet of a nonwoven fabric, a liquid-permeable plastic sheet, or the like; and an absorber composed of cotton-like pulp or the like interposed therebetween.

In such types of absorbent articles, in order to prevent excreted body fluid from leaking from the groin portion, three-dimensional gathers standing on the top surface side in various shapes along the longitudinal direction of the absorbent articles are formed. Examples of the sanitary napkin having a pair of three-dimensional gathers on either side on the top surface side are disclosed in, for example, JP-A-2001-145667; JP-A-2001-95842; JP-A-2002-656; and JP-A-64-68503.

However, the three-dimensional gathers shown in the above documents are formed on either side so as to correspond to the body fluid excretion portions, and they have a problem that they cannot properly prevent side leakage of body fluid, for example, excreted when a person lies on her back in bed, that temporarily flows to the buttock side and then diffuses laterally.

Accordingly, the following JP-A-2006-280580 and JP-A-2006-280583 disclose absorbent articles additionally provided with three-dimensional gathers on the buttock side. Specifically, the absorbent article according to JP-A-2006-280580 has front portion side three-dimensional gathers that stand on the top surface side by means of the contractive force of an elastic stretchable member on either side on the top surface side so as to correspond to the body fluid excretion portion of the absorbent article and also has back portion side three-dimensional gathers that stand on the top surface side by means of the contractive force of an elastic stretchable member on either side on the top surface side at the back portion of the absorbent article, so that non-standing portions are present between the front portion side three-dimensional gathers and the back portion side three-dimensional gathers. The absorbent article according to JP-A-2006-280583 has two sets of three-dimensional gather components each disposed over the longitudinal direction on either side on the top surface side of the absorbent article. The three-dimensional gather components of one of the two sets are configured so as to stand on the top surface side by means of the contractive force of an elastic stretchable members at portions corresponding to the body fluid excretion portion, and the three-dimensional gather components of the other of the two sets are configured so as to stand on the top surface side by means of the contractive force of an elastic stretchable member at portions corresponding to the buttock side.

However, in the three-dimensional gathers according to JP-A-2006-280580, though body shapes at the body liquid excretion portion and the buttock side portion are absolutely different from each other, the three-dimensional gathers disposed at the body liquid excretion portion and the buttock side portion have the same shapes. In particular, the effect of the three-dimensional gathers for preventing the flow at the buttock side portion is not sufficiently obtained. In the three-dimensional gathers according to JP-A-2006-280583, the three-dimensional gathers are formed so as to stand to form a dogleg-shaped cross section at the body fluid excretion portion and so as to stand in a linear fashion toward the outside at the buttock side portion. In particular, though it is possible to make the three-dimensional gathers fit to the curves of the buttocks at the buttock side, since two sets of three-dimensional gather components are provided so that one set forms three-dimensional gathers at the body fluid excretion portion and the other set forms three-dimensional gathers at the buttock side, for example, there is a problem in that the amount of the member forming the three-dimensional gathers is twice compared to usual one.

Figure 11:
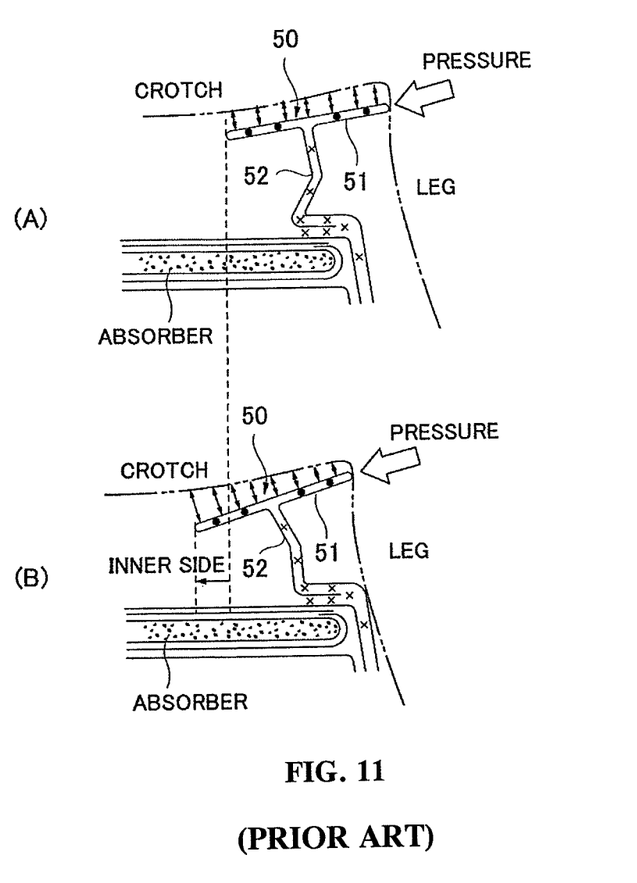
FIG. 11 includes schematic views (A) and (B) illustrating wearing process of a conventional absorbent article.

On the other hand, as shown in JP-A-2002-656, in the three-dimensional gather having a T-shaped cross section having a base wall portion standing from the surface of an absorbent article and inward and outward protrudes protruding toward the inside and the outside, respectively, of the absorbent article from the upper portion of the base wall portion, as shown in FIG. 11, since the outward protrude 51 that comes into contact with the crotch portion of a wearer is formed by laterally protruding from the base wall portion 52 being the standing portion of the three-dimensional gather, when the absorbent article is worn, the groin portion presses the outward protrude 51 to make the whole three-dimensional gather 50 fall down on the surface of the absorber as shown in (B) of FIG. 11. Similarly, this problem is likely caused in the three-dimensional gather having a Σ-shaped cross section described in JP-A-2001-145667 by that the skin patch portion is pressed and in the three-dimensional gather having a dogleg-shaped cross section described in JP-A-2001-95842 by that the folding point of the dogleg shape is pressed.

In the state in that the three-dimensional gather falls down on the absorber surface, the absorbent area is reduced to prevent the excreted body fluid from being absorbed by the absorber, which has a problem to cause side leakage of the body fluid moving along the three-dimensional gather, although the absorber still has an absorbing ability. Furthermore, as shown in FIG. 11(B), if the protrude portion falls down on the absorber surface, the distance from the crotch becomes ununiform to deteriorate fitting feeling and to cause leakage of body fluid.

SUMMARY OF THE INVENTION

Accordingly, a first object of the present invention is to form three-dimensional gathers that have different cross-section shapes in the body fluid excretion portion and the buttock side portion and fit to the body shape of each portion to give highly comfortable fitting feeling by a pair of the three-dimensional gathers disposed on either side over the longitudinal direction.

A second object is to improve fitting of three-dimensional gathers, to make the absorber reliably absorb body fluid without causing a reduction in absorbent area, and to reliably prevent side leakage by the flow-preventing effect.

In order to achieve the above-mentioned objects, the present invention, according to a first aspect, provides an absorbent article including a liquid-permeable top sheet, a back sheet, an absorber interposed therebetween, and three-dimensional gathers disposed along the longitudinal direction on either side on the use surface side, wherein the three-dimensional gathers are each made of a sheet folded in four, in a folded state, by folding the sheet extending from the lateral side of the absorbent article toward the center side direction at a first folding portion folded back toward the lateral side on a central side position, at a second folding portion folded back toward the center side direction on a lateral side position subsequent to the first folding portion, and a third folding portion folded back toward the lateral side on a central side position subsequent to the second folding portion so that a first folding back surface, a second folding back surface, a third folding back surface, and a fourth folding back surface are formed in this order from the lower layer side and so that the second folding portion is positioned on the outer side than the outward side end of the fourth folding back surface, and at least the third folding back surface and the fourth folding back surface stand so as to form an approximately dogleg-shaped cross section in a predetermined range containing the body fluid excretion portion in the longitudinal direction of the absorbent article; and the second to fourth folding back surfaces are bonded to one another in the buttock side portion of the absorbent article and stand linearly in an oblique manner toward the outer side direction using the first folding portion as the standing base point.

In the invention according to the first aspect, the three-dimensional gather is configured so that a sheet extending from the lateral side of the absorbent article toward the center side direction is folded in four by folding the sheet at a first folding portion folded back toward the lateral side on a central side position, at a second folding portion folded back toward the center side direction on a lateral side position subsequent to the first folding portion, and a third folding portion folded back toward the lateral side on a central side position subsequent to the second folding portion so that a first folding back surface, a second folding back surface, a third folding back surface, and a fourth folding back surface are formed in this order from the lower layer side and so that the sheet is folded in a state in that the second folding portion is positioned on the outer side than the outward side end of the fourth folding back surface; and at least the third folding back surface and the fourth folding back surface stand so as to form an approximately dogleg-shaped cross section in a predetermined range containing the body fluid excretion portion in the longitudinal direction of the absorbent article, and the second to fourth folding back surfaces are bonded to one another in the buttock side portion of the absorbent article and stand linearly in an oblique manner toward the outer side direction using the first folding portion as the standing base point.

Therefore, in the predetermined range containing the body fluid excretion portion in the longitudinal direction, the fourth folding back surface of the three-dimensional gather stands so as to come into contact with the crotch portion of a wearer, and, in the buttock side portion, the three-dimensional gather standing linearly in an oblique manner fit along the curve of the buttocks. Thus, it is possible to form three-dimensional gathers that fit to the body shapes of respective regions and give highly comfortable fit by the pair of three-dimensional gathers provided on either side along the longitudinal direction.

Since the sheet is folded in the state in that the second folding portion is positioned on the outer side than the outward side end of the fourth folding back surface, the position of the free end (outward side end of the fourth folding back surface) of the three-dimensional gather in the predetermined range containing the body fluid excretion portion in the longitudinal direction differs from that of the free end (second folding portion) of the three-dimensional gather in the buttock side portion so that the free end of the three-dimensional gather in the buttock side portion is positioned relatively on the outer side. That is, in the predetermined range containing the body fluid excretion portion in the longitudinal direction, the body contacting surface (fourth folding back surface) having a relatively narrow width reliably comes into contact with the crotch portion, and, at the same time, in the buttock side portion, the body contacting surface (laminated layer portion of the second to fourth folding back surfaces) having a relatively wide width comes into contact with the body to reliably prevent side leakage.

The present invention, according to a second aspect, provides an absorbent article including a liquid-permeable top sheet, a back sheet, an absorber interposed therebetween, and three-dimensional gathers disposed along the longitudinal direction on either side on the use surface side, wherein the three-dimensional gathers are each made of a sheet folded in four, in a folded state, by folding the sheet extending from the lateral side of the absorbent article toward the center side direction at a first folding portion folded back toward the lateral side on a central side position, at a second folding portion folded back toward the center side direction on a lateral side position subsequent to the first folding portion, and a third folding portion folded back toward the lateral side on a central side position subsequent to the second folding portion so that a first folding back surface, a second folding back surface, a third folding back surface, and a fourth folding back surface are formed in this order from the lower layer side and so that the second folding portion is positioned on the outer side than the outward side end of the fourth folding back surface, in a predetermined range containing the body fluid excretion portion in the longitudinal direction of the absorbent article, the relatively inner side portions of the second folding back surfaces of the three-dimensional gathers are bonded to the use surface side over the longitudinal direction; other folding back surfaces are not bonded; the three-dimensional gathers each have a side standing portion that stands from the side edge portion of the absorber or proximity thereof and a skin contacting portion having a predetermined width and formed sequentially from the end of the side standing portion so as to be approximately horizontal with respect to the surface of the absorbent article or so as to incline toward the center side; and the three-dimensional gather stands in a state in that the side standing portion is positioned on the outer side than the outward side end of the skin contacting portion, and in the buttock side portion of the absorbent article, the first folding back surface and the second folding back surface are not bonded to each other; the second folding back surface and the third folding back surface are bonded to each other; the third folding back surface and the fourth folding back surface are bonded to each other; and the three-dimensional gather stands linearly in an oblique manner toward the outer side direction using the first folding portion as the standing base point.

In the present invention of the second aspect, a preferred specific embodiment of the three-dimensional gather is shown. That is, in the three-dimensional gather in a predetermined range containing the body fluid excretion portion in the longitudinal direction, the relatively inner side portions of the second folding back surfaces are bonded to the use surface side over the longitudinal direction; other folding back surfaces are non-bonded; the three-dimensional gathers each have a side standing portion that stands from the side edge portion of the absorber or proximity thereof and a skin contacting portion having a predetermined width and formed sequentially from the end of the side standing portion so as to be approximately horizontal with respect to the surface of the absorbent article or so as to incline toward the center side; and the three-dimensional gather stands in a state in that the side standing portion is positioned on the outer side than the outward side end of the skin contacting portion. On the other hand, in the three-dimensional gather in the buttock side portion, the first folding back surface and the second folding back surface are not bonded to each other; the second folding back surface and the third folding back surface are bonded to each other; the third folding back surface and the fourth folding back surface are bonded to each other; and the three-dimensional gather stands linearly in an oblique manner toward the outer side direction using the first folding portion as the standing base point.

In particular, since the three-dimensional gather in the predetermined range containing the body fluid excretion portion in the longitudinal direction is configured so that the side standing portion is positioned on the outer side than the outward side end of the skin contacting portion, the skin contacting portion is pressed by the groin portion when the absorbent article is worn to prevent the entire three-dimensional gathers from falling down on the surface of the absorber. Therefore, body fluid is reliably absorbed by the absorber, without causing a reduction in absorbent area. Due to the above-mentioned configuration, since it is possible to bring the side standing portions of the three-dimensional gathers into contact with the legs of a wearer and also to bring the skin contacting portion into contact with the crotch, the effect of the three-dimensional gathers to prevent body fluid from flowing can be sufficiently achieved, which makes it possible to reliably prevent side leakage of the body fluid.

The present invention, according to a third aspect, provides the absorbent article according to the second aspect, wherein the side standing portion and the skin contacting portion are each provided with one ore more lines of an elastic stretchable member along the longitudinal direction of the absorbent article.

In the invention of the third aspect, in order to enhance the fitting feeling due to the side standing portion and the skin contacting portion, the elastic stretchable member is disposed in each portion.

The present invention, according to a fourth aspect, provides the absorbent article according to either the second or third aspect, wherein the color of the elastic stretchable member of the side standing portion differs from that of the elastic stretchable member of the skin contacting portion.

In the invention of the fourth aspect, in order to emphasize recognition by a user for the effect of the two surfaces, that is, the side standing portion and the face-contacting portion, the elastic stretchable members are provided with colors.

ADVANTAGEOUS EFFECTS OF INVENTION

As described in detail above, according to the present invention, the pair of three-dimensional gathers disposed on either side along the longitudinal direction can be formed so as to have different cross-section shapes in the body fluid excretion portion and the buttock side portion and so as to fit to the body shape of each portion and give highly comfortable fitting feeling. In addition, it is possible to improve the fitting of the three-dimensional gathers, to make the absorber reliably absorb body fluid without causing a reduction in absorbent area, and to reliably prevent side leakage by an effect of the three-dimensional gathers interrupting the flow of body fluid.

DETAILED DESCRIPTION OF THE INVENTION

Embodiments of the present invention will be described in detail below with reference to the drawings.

Figure 1:
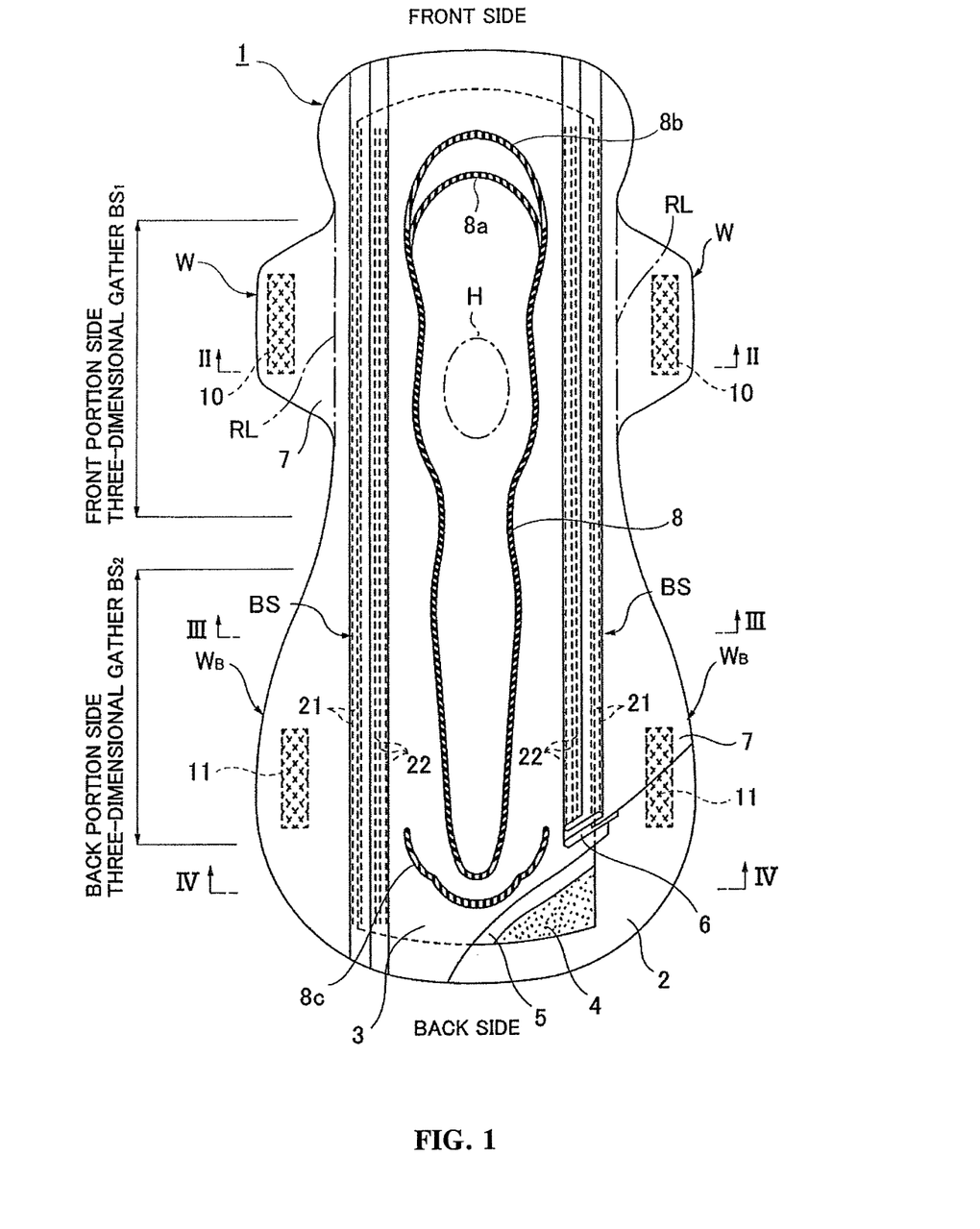
FIG. 1 is a view from above the sanitary napkin 1 of the present invention and which shows aspects of the construction thereof throughout.

The sanitary napkin 1 is mainly composed of a liquid-impermeable back sheet 2 made of, for example, a polyethylene sheet; a liquid-permeable top sheet 3 that allows, for example, menstrual blood or vaginal discharge to rapidly permeate therethrough; an absorber 4 interposed between the both sheets 2 and 3 and made of, for example, cotton pulp or synthetic pulp; a crepe paper 5 surrounding the absorber 4 for maintaining the shape of the absorber 4 and enhancing the diffusing ability of the absorber 4; and three-dimensional gathers BS and BS forming a pair of three-dimensional gathers $BS_1$ on either side on the front side in a predetermined area containing the body fluid excretion portion H in the longitudinal direction and forming a pair of three-dimensional gathers $BS_2$ on either side on the back side in the buttock side portion. In the front and back end portions of the circumference of the absorber 4, the outer ends of the liquid-impermeable back sheet 2 and the liquid-permeable top sheet 3 are bonded with an adhesive, such as a hot-melt adhesive, or by bonding means, such as heat sealing. In the both side end portions of the circumference of the absorber 4, the liquid-impermeable back sheet 2 protruding sideward than the absorber 4 and side nonwoven fabric 7 are bonded with an adhesive, such as a hot-melt adhesive, or by bonding means, such as heat sealing. These laminated sheet portions of the liquid-impermeable back sheet 2 and the side nonwoven fabric 7 form wing-like flaps W and W protruding sideward and second wing-like flaps $W_B$ and $W_B$ positioning on the buttock portion side than the wing-like flaps.

The liquid-impermeable back sheet 2 is made of a sheet material having at least a waterproof property, such as polyethylene, but recently, from the viewpoint of preventing stuffy feel, a material having moisture permeability tends to be used. As such a waterproof and moisture-permeable sheet material, a micro-porous sheet that is prepared by melt-kneading an inorganic filler in an olefin-based resin, such as polyethylene or polypropylene, to form a sheet and then uniaxially or biaxially extending it is preferably used. On the non-use surface side (outer surface) of the liquid-impermeable back sheet 2, one or more lines of adhesive layers (not shown) are provided for fixing the sanitary napkin 1 to undergarment when it is worn. As the liquid-impermeable back sheet 2, a polymer laminated nonwoven fabric in which a plastic film and a nonwoven fabric are laminated may be used.

The liquid-permeable top sheet 3 is preferably made of a porous or nonporous nonwoven fabric or a porous plastic sheet. The fibrous base material constituting the nonwoven fabric may be, as well as a synthetic fiber such as an olefin-based (such as polyethylene or polypropylene), polyester-based, or polyamide-based synthetic fiber, a recycled fiber such as rayon or cupra, or a natural fiber such as cotton, and a nonwoven fabric prepared by an arbitrary processing method such as spunlacing, spunbonding, thermal bonding, melt blowing, or needle punching can be used. Among these processing methods, the spunlacing is excellent in flexibility and drape forming, and the thermal bonding is excellent in bulk and softness. When the liquid-permeable top sheet 3 is provided with a large number of pores, it can rapidly absorb menstrual blood, vaginal discharge, or the like (hereinafter collectively referred to as body fluid), and is therefore excellent in dry feeling.

The absorber 4 interposed between the liquid-impermeable back sheet 2 and the liquid-permeable top sheet 3 is constituted of, for example, fluff-like pulp and an absorbent polymer. The absorbent polymer is mixed in the pulp constituting the absorber as, for example, granular powder. Examples of the pulp include those composed of cellulose fibers such as chemical pulp made from wood and melting pulp, and artificial cellulose fibers such as rayon and acetate. Softwood pulp has a longer fiber length than hardwood pulp and is preferably used in the light of function and cost. As in this embodiment, crepe paper 5 surrounding the absorber 4 is provided, as a matter of course, the crepe paper 5 is interposed between the liquid-permeable top sheet 3 and the absorber 4, and the crepe paper 5 excellent in absorbability allows body fluid to rapidly diffuse and prevents returning back of the menstrual blood and so on.

The surface of the sanitary napkin 1 is provided with a compressed groove 8 that is long and narrow in the longitudinal direction of the sanitary napkin 1 and is closed in the circumferential direction. On the front side of the front end portion 8a of the compressed groove 8, a semicircular compressed groove 8b is disposed so as to be connected to the front end portion with a gap therebetween and so as to form a crescent-shaped reservoir pocket together with the compressed groove 8a at the front end portion. As a result, the front end portion of the sanitary napkin 1 fits to the skin by inflecting the front end portion into a ship front like shape and serves as a reservoir to prevent outflow of body fluid even if the body fluid flows toward the front end side. On the other hand, on the back side portion of the napkin 1, a combined-semicircular compressed groove 8c is independently provided and serves as a reservoir to prevent outflow of body fluid even if the body fluid flows toward the back portion side. The compressed grooves 8, 8a, 8b, and 8c can be formed by arbitrary means, such as embossing with heat and/or pressure, ultrasound, or combination thereof.

Figure 2:
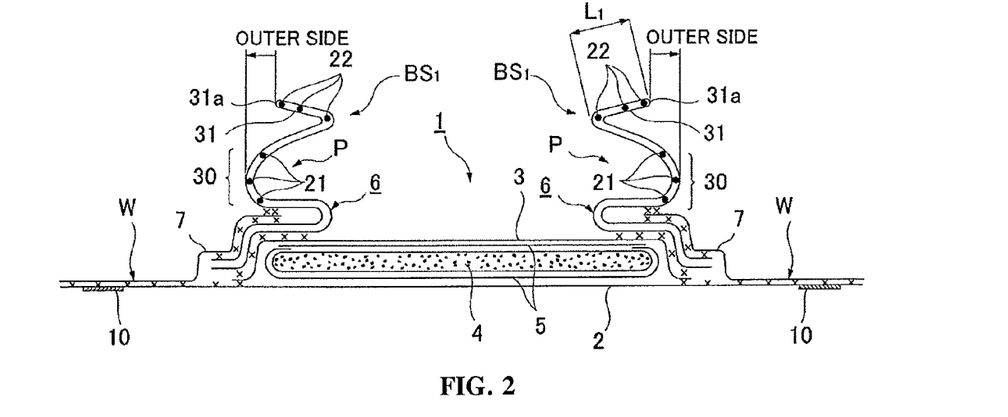
FIG. 2 is a transversal cross-sectional view (fragmentary view taken along the line II-II of FIG. 1).
Figure 3:
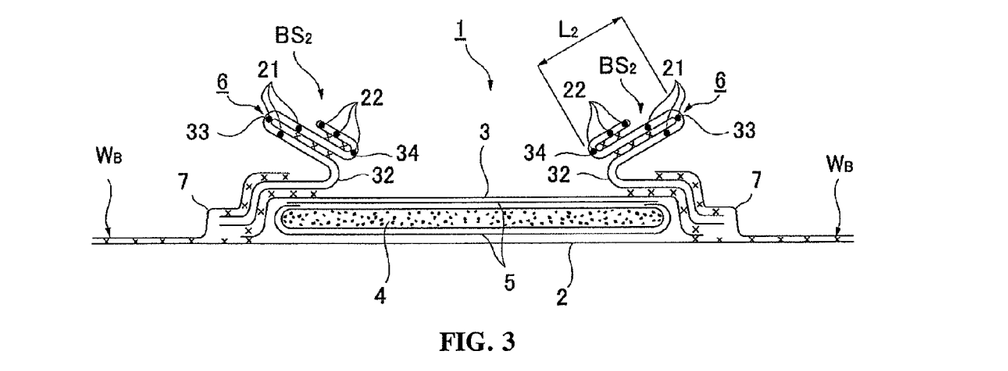
FIG. 3 is a transversal cross-sectional view (fragmentary view taken along the line III-III of FIG. 1).

The width size of the liquid-permeable top sheet 3 shown in the drawing is slightly longer than the width of the absorber 4 to merely cover the absorber 4, as shown in the transversal cross-sectional views of FIGS. 2 and 3. The three-dimensional gathers BS and BS are made of three-dimensional gather-forming nonwoven fabric 6, which is different from that of the liquid-permeable top sheet 3. On the outsides of the three-dimensional gathers BS and BS, the side nonwoven fabric 7 is laminated on the top surface side of the liquid-impermeable back sheet 2. The three-dimensional gather-forming nonwoven fabric 6 and the side nonwoven fabric 7 are constituted of nonwoven materials properly subjected to water repellency treatment or hydrophilic treatment, depending on the purpose, for example, prevent infiltration of menstrual blood, vaginal discharge, or the like or enhancement of texture. Such nonwoven fabric 6 and 7 can be formed by arbitrarily processing a natural fiber, a synthetic fiber, or a recycled fiber as a base material, but is preferably made of a nonwoven fabric provided with breathability by reducing the basis weight, in order to eliminate a stiff feeling and prevent stuffy feel. Specifically, a nonwoven fabric prepared so as to have a basis weight of 13 to 23 $g/m^2$ is desirable, and preferably used is a water repellency-treated nonwoven fabric coated with, for example, a silicone, paraffin, or alkyl chromic chloride-based water repellent, in order to certainly prevent permeation of body fluid.

In the side nonwoven fabric 7, as shown in FIGS. 2 and 3, the outer side portions are bonded over a range to the outer edges of the liquid-impermeable back sheet 2 with an adhesive such as a hot melt adhesive, and the laminated sheet portions of the side nonwoven fabric 7 and the liquid-impermeable back sheet 2 form a pair of wing-like flaps W and W on either side at the lateral positions of the absorber approximately corresponding to the body fluid excretion portion and form second wing-like flaps $W_B$ and $W_B$ at the positions on the buttock side than the wing-like flaps W and W. The wing-like flaps W and W and the second wing-like flaps $W_B$ and $W_B$ include adhesive layers 10 and 11 on the out surface sides. When the napkin is attached to shorts, the wing-like flaps W and W are folded to the opposite side at the positions of folding lines RL and are fixed by wrapping around the crotch portion of the shorts.

As the three-dimensional gather-forming nonwoven fabric 6 constituting the three-dimensional gather BS, a doubly folded sheet is used, and a plurality of string-like elastic stretchable members 21 and 22 are arranged at predetermined positions in the middle portion in the height direction inside the double sheet and are fixed at the both ends or appropriate positions thereof in the longitudinal direction. In a predetermined range containing the body fluid excretion portion H in the longitudinal direction, as shown in FIG. 2, a pair of the front portion side three-dimensional gathers $BS_1$ is formed on either side, and, as shown in FIG. 3, a pair of back portion side three-dimensional gathers $BS_2$ is formed on the buttock side portion.

The structure of the three-dimensional gather BS is described below in detail.

Figure 5:
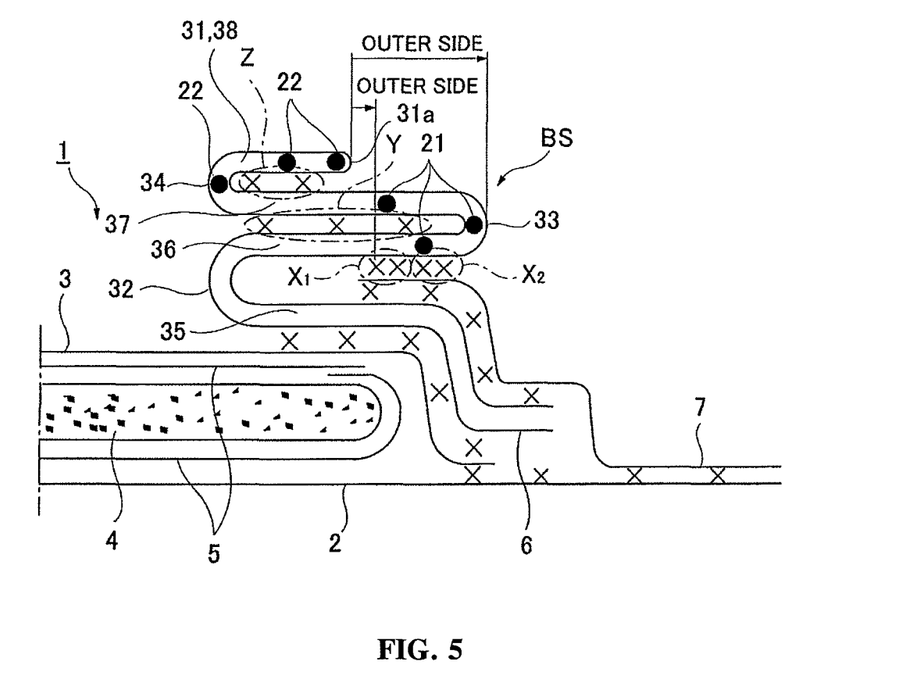
FIG. 5 is a main enlarged transversal cross-sectional view illustrating a state in that three-dimensional gather BS is folded.

The three-dimensional gather BS according to the present invention is, as shown in FIG. 5, made of a sheet folded in four, in a folded state, by folding the sheet extending from the lateral side of the napkin 1 toward the center side direction at a first folding portion 32 folded back toward the lateral side on a central side position, at a second folding portion 33 folded back toward the center side direction on a lateral side position subsequent to the first folding portion 32, and a third folding portion 34 folded back toward the lateral side on a central side position subsequent to the second folding portion 33 so that a first folding back surface 35, a second folding back surface 36, a third folding back surface 37, and a fourth folding back surface 38 are formed in this order from the lower layer side. Here, the fourth folding back surface 38 constitutes a skin contacting portion 31.

Furthermore, as shown in FIG. 5, the second folding portion 33 is positioned at the outer side than the outward side end 31a of the fourth folding back surface 38 (skin contacting portion 31), and the second folding back surface 36 is bonded to the use surface side at the outer side position than the outward side end 31a of the fourth folding back surface 38 (skin contacting portion 31). In the example shown in the drawing, since the side nonwoven fabric 7 extends to the middle portion on the outer surface side of the first folding back surface 35, the second folding back surface is bonded to the upper surface of the side nonwoven fabric 7. When the side nonwoven fabric 7 does not extend to this bonding portion, the second folding back surface may be bonded to the first folding back surface 35.

In front portion side three-dimensional gathers $BS_1$ formed in the predetermined range containing the body fluid excretion portion H in the longitudinal direction of the napkin 1, as shown in FIG. 2, the relatively inner side portions (at bonding region $X_1$ discussed below) of the second folding back surfaces 36, which are positioned further to the outside of the absorbent article than the outer side end of the fourth folding back surface, are bonded to the use surface side over the longitudinal direction, and other folding back surfaces are non-bonded. The three-dimensional gathers $BS_1$ each have a side standing portion 30 that stands from the side edge portion of the absorber 4 or proximity thereof and a skin contacting portion 31 having a predetermined width and formed sequentially from the end of the side standing portion 30 so as to be approximately horizontal with respect to the surface of the napkin 1 or so as to incline toward the center side. The three-dimensional gather stands in a state in that the side standing portion 30 is positioned on the outer side than the outward side end of the skin contacting portion 31. The side standing portion 30 and the skin contacting portion 31 are provided with one or more, in the example shown in the drawing, three, string-like elastic stretchable members 21 and 22, respectively, along the longitudinal direction of the sanitary napkin 1.

On the other hand, in each back portion side three-dimensional gathers $BS_2$ formed in the buttock side portion of the napkin 1, the first folding back surface 35 and the second folding back surface 36 are not bonded to each other; the second folding back surface 36 and the third folding back surface 37 are bonded to each other; the third folding back surface 37 and the fourth folding back surface 38 are bonded to each other; and the three-dimensional gather stands linearly in an oblique manner toward the outer side direction using the first folding portion 32 as the standing base point.

Accordingly, in the predetermined range containing the body fluid excretion portion H in the longitudinal direction, the fourth folding back surface 38 of the three-dimensional gather stands so as to come into contact with the crotch portion of a wearer, and, in the buttock side portion, the three-dimensional gather standing linearly in an oblique manner fits along the curve of the buttocks. Therefore, the three-dimensional gathers can be formed so as to fit to the body shape of each portion and give highly comfortable fitting feeling by the pair of three-dimensional gathers BS and BS disposed on either side over the longitudinal direction.

In addition, since the three-dimensional gather is folded so that the second folding portion 33 is positioned on the outer side than the outward side end of the fourth folding back surface 38, the position of the free end (outward side end of fourth folding back surface 38) of the front portion side three-dimensional gather $BS_1$ in the predetermined rang containing the body fluid excretion portion H in the longitudinal direction differs from the position of the free end (second folding portion 33) of the back portion side three-dimensional gathers $BS_2$ in the buttock side portion so that the free end of the back side portion three-dimensional gathers $BS_2$ in the buttock side portion is relatively positioned on the outer side. As a result, in the predetermined range containing the body fluid excretion portion H in the longitudinal direction, the body contacting surface (fourth folding back surface 38) having a relatively narrow width (width: $L_1$) reliably comes into contact with the crotch portion, and at the same time, in the buttock side portion, the body contacting surface (laminated layer portion of the second to fourth folding back surfaces) having a relatively wide width (width: $L_2$) comes into contact with the body to reliably prevent side leakage.

Figure 4:
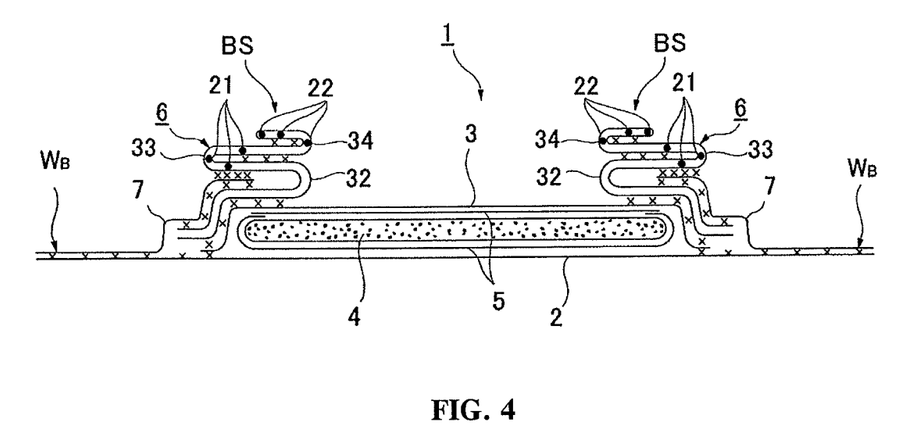
FIG. 4 is a transversal cross-sectional view (fragmentary view taken along the line IV-IV of FIG. 1).

In the area on the front side than the front portion side three-dimensional gather $BS_1$ and the area on back side than the back portion side three-dimensional gather $BS_2$, as shown in FIG. 4, all surfaces of the first folding back surface 35, the second folding back surface 36, the third folding back surface 37, and the fourth folding back surface 38 are bonded into a folded state.

Figure 6:
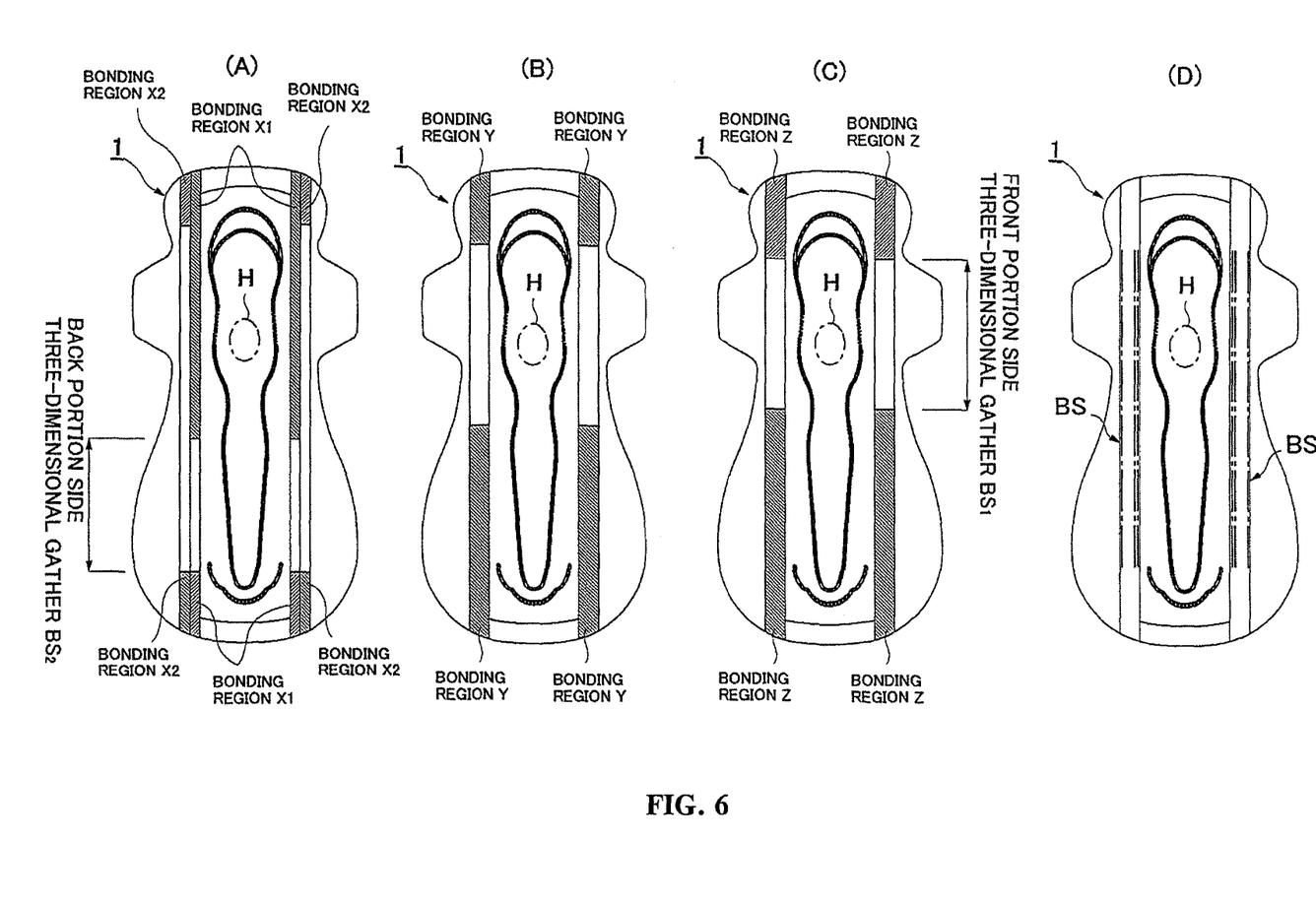
FIG. 6 includes views illustrating (A) a facing state of a first folding portion 35 and a second folding portion 36, (B) a facing state of the second folding portion 36 and a third folding portion 37, (C) a facing state of the third folding portion 37 and a fourth folding portion 38, and (D) arrangement zones of elastic stretchable members 21 and 22.

Then, the bonding state of each folding back surface, when the predetermined range containing the body fluid excretion portion H in longitudinal direction and the buttock side portion are respectively provided with the three-dimensional gathers $BS_1$ and $BS_2$ having different cross-sectional views from each other by the three-dimensional gather-forming nonwoven fabric 6 disposed in the folded state on both sides, will be described based on FIG. 6.

In the folded status shown in FIG. 5, for each bonding region, regarding the facing surfaces of the first folding back surface 35 and the second folding back surface 36, on the outer side than the outward side end 31a of the fourth folding back surface 38 in the second folding back surface 36, the relatively inner portion is defined as a bonding region $X_1$, and the relatively outer portion is defined as a bonding region $X_2$. The facing surfaces of the second folding back surface 36 and the third folding back surface 37 are referred to as bonding region Y, and the facing surfaces of the third folding back surface 37 and the fourth folding back surface 38 are referred to as bonding region Z.

FIG. 6(A) shows a bonding state of the first folding back surface 35 and the second folding back surface 36, FIG. 6(B) shows a bonding state of the second folding back surface 36 and the third folding back surface 37, and FIG. 6(C) shows a bonding state of the third folding back surface 37 and the fourth folding back surface 38.

In the bonding region X in the facing surfaces of the first folding back surface 35 and the second folding back surface 36, as shown in FIG. 6(A), in order to place the standing position of the three-dimensional gather $BS_1$ on the outer side of the outward side end 31a of the skin contacting portion 31, as shown in FIG. 6(A), the bonding region $X_1$ being the relatively inner portion on the outer side than the outward side end 31a of the fourth folding back surface 38 in the second folding back surface 36 is non-bonded in the zone of the back portion side three-dimensional gather $BS_2$ and is bonded to the use surface side in the remaining range over the entire longitudinal direction of the three-dimensional gather BS. In addition, the bonding region $X_2$ being the relatively outer portion is bonded only at the front end and the back end excluding the range from the front portion side three-dimensional gather $BS_1$ zone (the front end+α) to the back portion side three-dimensional gather $BS_2$.

In the bonding region Y in the facing surfaces of the second folding back surface 36 and the third folding back surface 37, as shown in FIG. 6(B), the zone that is slightly larger than the zone of the front portion side three-dimensional gather $BS_1$ in the front and back directions is non-bonded, and the zone other than the above is bonded to each other.

The bonding region 2 in the facing surfaces of the third folding back surface 37 and the fourth folding back surface 38, as shown in FIG. 6(C), the front portion side three-dimensional gather $BS_1$ zone is non-bonded, and the zone other than the above is bonded to each other.

FIG. 6(D) shows the zone where the string-like elastic stretchable members 21 and 22 are arranged, and the arrangement is formed almost over from the front portion side three-dimensional gather $BS_1$ zone to the back portion side three-dimensional gather $BS_2$ zone.

As described above, by bonding the folding back surfaces to each other, it is possible to form the three-dimensional gathers $BS_1$ and $BS_2$ so that the cross-section shapes are different in the predetermined range containing the body fluid excretion portion H in the longitudinal direction and the buttock side portion.

Figure 7:
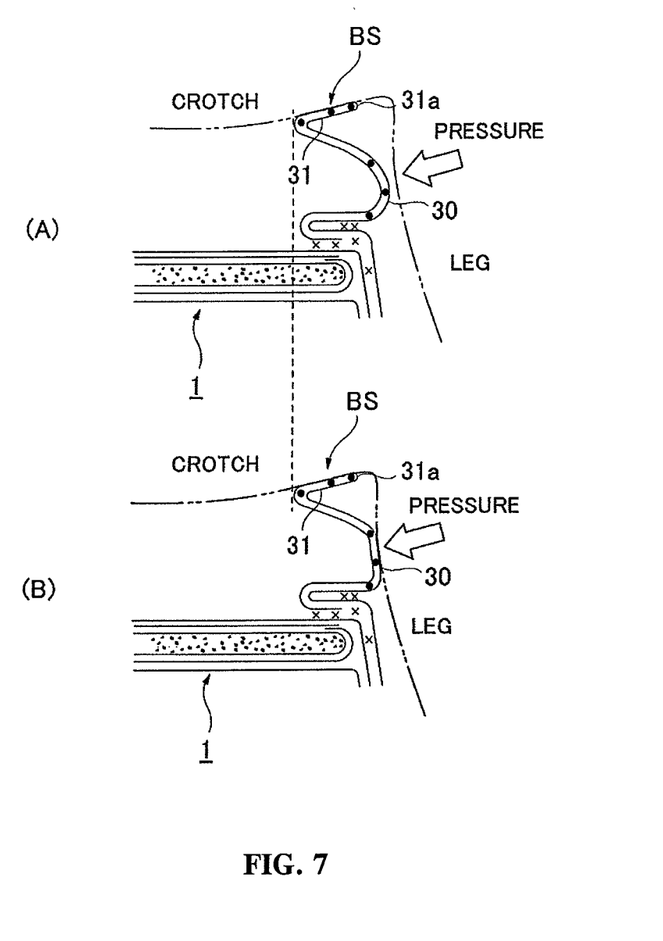
FIG. 7 includes schematic views (A) and (B) illustrating wearing process of the sanitary napkin 1.

According to the thus-configured three-dimensional gather BS, in the predetermined range containing the body fluid excretion portion H in the longitudinal direction, as shown in FIG. 7(A), when the sanitary napkin 1 is worn, the groin of the wearer does not come into contact with the outward side end 31a of the skin contacting portion 31 of the three-dimensional gather $BS_1$, and the three-dimensional gather BS hardly falls down to the inner side. In addition, since the side standing portion 30 is disposed on the outer side than the outward side end 31a of the skin contacting portion 31, as shown in FIG. 7(B), the side standing portion 30 serves as a buffer receiving pressure, even if the side standing portion 30 is pressed by the leg, preventing the skin contacting portion 31 from being influenced by the pressure or minimizing the influence. Therefore, the skin contacting portion 31 is prevented from falling down to the absorber surface side.

Since two surfaces, that is, the side standing portion 30 and the skin contacting portion 31, are brought into contact with the skin, the area of three-dimensional gather that comes into contact with the skin can be increased, compared to conventional products, to enhance the fitting feeling of the three-dimensional gather and reliably prevent side leakage of body fluid.

Figure 8:
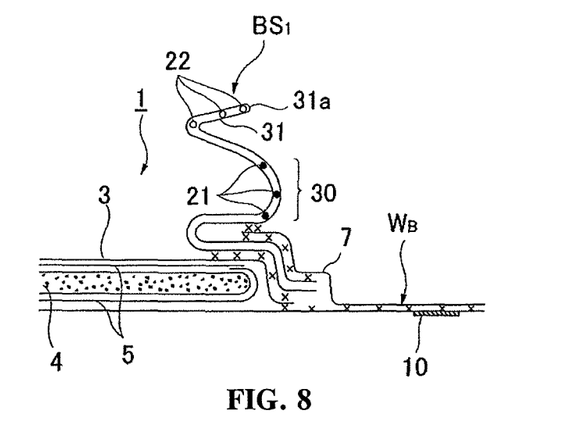
FIG. 8 is a main enlarged transversal cross-sectional view illustrating a color combination state of the elastic stretchable members 21 and 22 provided in a side standing portion 30 and a skin contacting portion 31.

Incidentally, the elastic stretchable members 21 and 22 disposed in the side standing portion 30 and the skin contacting portion 31 are preferably provided with different colors, so that a user can visibly recognize the effect (the direction of fitting is different) of the two surfaces. For example, in the example shown in FIG. 8, the elastic stretchable members 22, . . . , and 22 disposed in the skin contacting portion 31 is white (○), and the elastic stretchable members 21, . . . , and 21 disposed in the side standing portion 30 is black (●).

Additional Aspects of the Present Invention are Described Hereinbelow.

Figure 9:
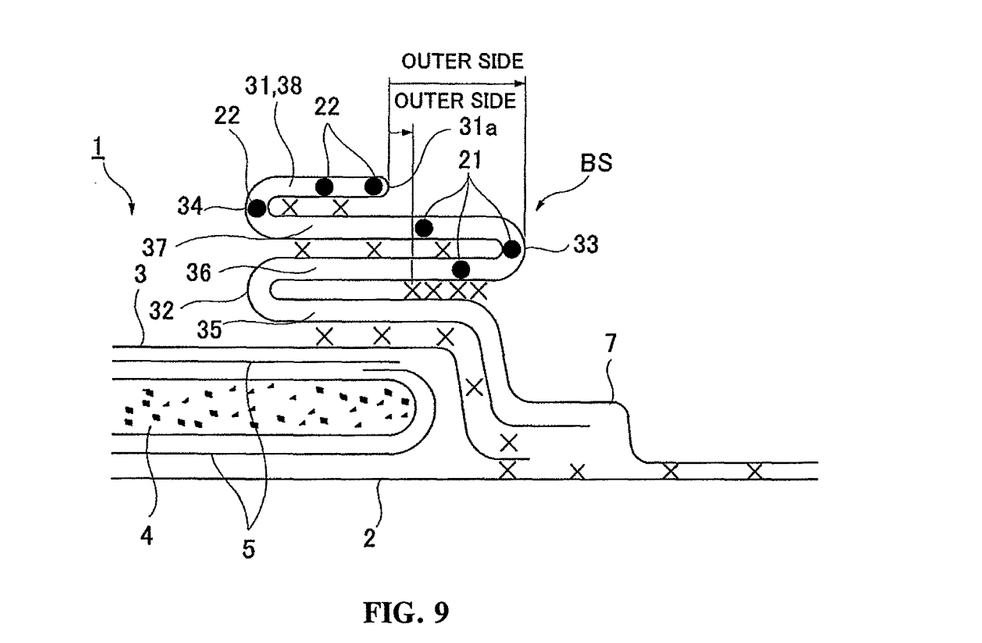
FIG. 9 is a main enlarged transversal cross-sectional view illustrating another embodiment of the three-dimensional gather BS.

(1) In the embodiment described above, the three-dimensional gather BS is made of a three-dimensional gather forming nonwoven fabric 6, which differs from the side nonwoven fabric 7. However, as shown in FIG. 9, the three-dimensional gather BS may be made of a double sheet portion extended from the inner side of the side nonwoven fabric 7.

Figure 10:
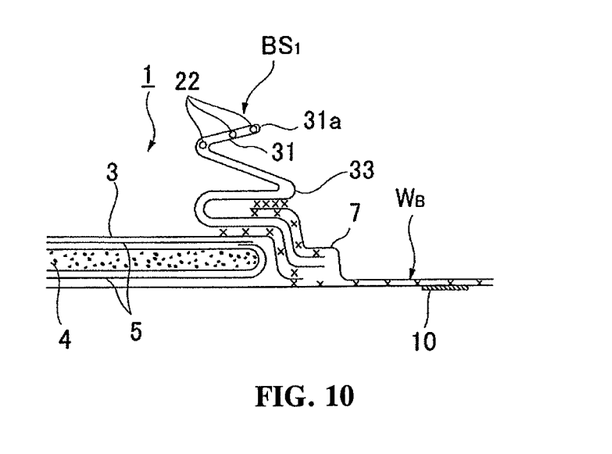
FIG. 10 is a main enlarged transversal cross-sectional view illustrating another embodiment of the three-dimensional gather BS.

(2) In the embodiment described above, the side standing portion 30 was provided on the front portion side three-dimensional gather $BS_1$, but, as shown in FIG. 10, the three-dimensional gather may be configured to stand using the second folding portion 33 as the standing base point so as to form an approximately dogleg-shaped cross section.

The invention claimed is:
1. An absorbent article, comprising:
a liquid-permeable top sheet;
a back sheet;
an absorber interposed therebetween; and
three-dimensional gathers disposed along the longitudinal direction on either side on a use surface side of the absorbent article so as to be disposed over a predetermined range in the longitudinal direction that includes a body fluid excretion portion, and over a buttock side portion,
the three-dimensional gathers each being made of a sheet folded in four, in a folded state, so that the sheet extending from the lateral side of the absorbent article is folded toward the center side direction thereof at a first folding portion folded back toward the lateral side on a central side position, at a second folding portion folded back toward the center side direction on a lateral side position subsequent to the first folding portion, and at a third folding portion folded back toward the lateral side on a central side position subsequent to the second folding portion so that a first folding back surface, a second folding back surface, a third folding back surface, and a fourth folding back surface are formed in this order from a lower layer side of the absorbent article and so that the second folding portion is positioned on an outer side outward of an outward side end of the fourth folding back surface, and
in the predetermined range in the longitudinal direction of the absorbent article containing the body fluid excretion portion, a respective inner side portion of the second folding back surfaces of the three-dimensional gathers is bonded to the use surface side of the absorbent article over the longitudinal direction thereof at a position that is located further to the outer side of the absorbent article than is the outer side end of the fourth folding back surface, folding back surfaces between the second folding back surface and the third folding back surface and between the third folding back surface and the fourth folding back surface are non-bonded to the use side surface of the absorbent article, and the three-dimensional gathers each have a side standing portion that stands from the side edge portion of the absorber or proximity thereof and a skin contacting portion having a predetermined width and formed sequentially from the end of the side standing portion so as to be approximately horizontal with respect to the surface of the absorbent article or so as to incline toward the center side, and the three-dimensional gather stands in a state so that the side standing portion is positioned on the outer side than an outward side end of the skin contacting portion, and
in a buttock side portion of the absorbent article, the first folding back surface and the second folding back surface are not bonded to each other, the second folding back surface and the third folding back surface are bonded to each other, the third folding back surface and the fourth folding back surface are bonded to each other, and laminated layer portions of the second to fourth folding back surfaces stand linearly in an oblique manner toward the outer side direction of the absorbent article using the first folding portion as a standing base point.

2. The absorbent article according to claim 1, wherein the side standing portion and the skin contacting portion are each provided with one or more line portions of an elastic stretchable member along the longitudinal direction of the absorbent article.

3. The absorbent article according to claim 1 or 2, wherein the color of the elastic stretchable member of the side standing portion differs from that of the elastic stretchable member of the skin contacting portion.

4. The absorbent article according to claim 1, wherein at least the third folding back surface and the fourth folding back surface stand so as to form an approximately dogleg-shaped cross section in the predetermined range containing the body fluid excretion portion in the longitudinal direction of the absorbent article.

* * * * *